United States Patent
Cosentino et al.

(10) Patent No.: US 8,166,820 B2
(45) Date of Patent: May 1, 2012

(54) METHOD FOR DETECTING A SONIC IMPRINT OF A THREE-DIMENSIONAL OBJECT AND RELATED APPARATUS

(75) Inventors: Pietro Lucio Cosentino, Palermo (IT); Gianluca Fiandaca, Palermo (IT); Paolo Messina, Palermo (IT); Raffaele Martorana, Palermo (IT); Patrizia Capizzi, Palermo (IT); Isaac Razo Amoroz, Palermo (IT)

(73) Assignees: Universita' Degli Studi Di Palermo, Palermo (IT); Diasis S.r.L., Palermo (IT)

( * ) Notice: Subject to any disclaimer, the term of this patent is extended or adjusted under 35 U.S.C. 154(b) by 362 days.

(21) Appl. No.: 12/449,383

(22) PCT Filed: Feb. 6, 2008

(86) PCT No.: PCT/EP2008/051461
§ 371 (c)(1),
(2), (4) Date: Aug. 5, 2009

(87) PCT Pub. No.: WO2008/095961
PCT Pub. Date: Aug. 14, 2008

(65) Prior Publication Data
US 2010/0089160 A1    Apr. 15, 2010

(30) Foreign Application Priority Data
Feb. 6, 2007 (IT) .............................. RM2007A0059

(51) Int. Cl.
*G01H 1/00* (2006.01)
(52) U.S. Cl. ........................................................ 73/579
(58) Field of Classification Search ........................ None
See application file for complete search history.

(56) References Cited

U.S. PATENT DOCUMENTS

2003/0041509 A1* 3/2003 Cutright et al. ................ 44/553
2005/0072234 A1   4/2005 Zhu et al.

FOREIGN PATENT DOCUMENTS
EP   0636881       2/1995
WO   WO0133183 A1  5/2001

* cited by examiner

*Primary Examiner* — Robert R Raevis
(74) *Attorney, Agent, or Firm* — Stetina Brunda Garred & Brucker

(57) ABSTRACT

Non invasive method used to detect a "sonic imprint" of three-dimensional objects, particularly suitable for the identification and monitoring of artworks, consisting in acquiring the vibrations caused by a source of elastic waves and using a set of detectors fixed in various predetermined points of the external surface of the object. An apparatus, cheap and simple to utilize, suitable to execute this method, is also described.

9 Claims, 2 Drawing Sheets

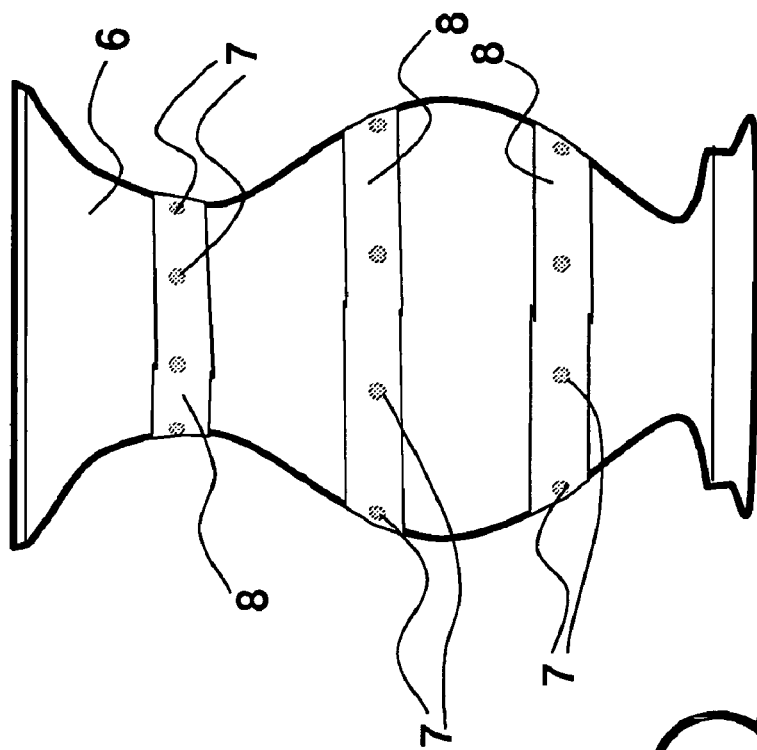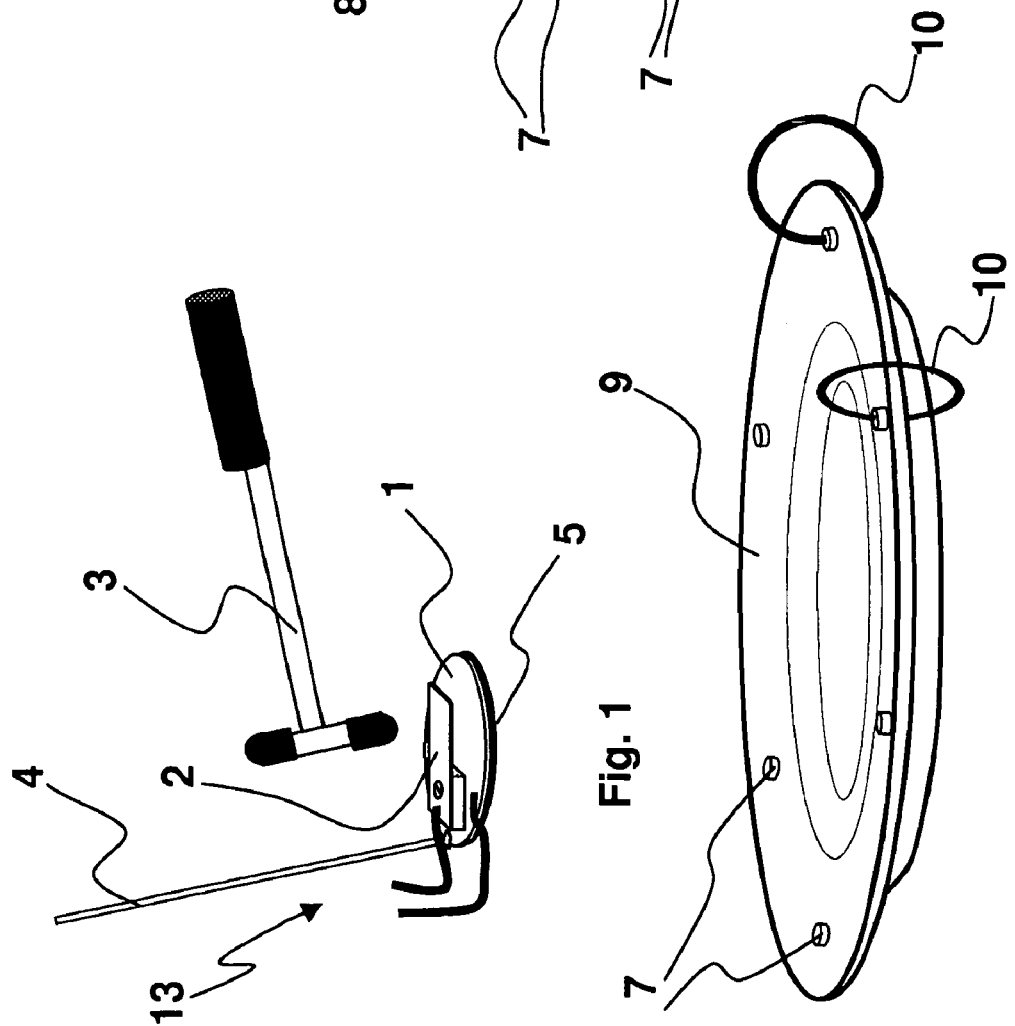

METHOD FOR DETECTING A SONIC IMPRINT OF A THREE-DIMENSIONAL OBJECT AND RELATED APPARATUS

FIELD OF THE INVENTION

This invention deals with a method for detecting a "sonic imprint" of three-dimensional objects, in particular artworks, and a related detecting apparatus.

STATE OF THE ART

Study and analysis of cultural goods (statues, vessels, pottery, brass objects, various furnishing, paintings, etc.) is more and more important and urgent, due to the abundance of cultural heritage in various countries as well as to the state of decay of most of the artworks.

Nowadays, a large number of artworks are transferred from one museum to another, and from one country to another, so that people all over the world can appreciate them. However, this can be very dangerous for a myriad reasons, not least for problems that could arise in connection with transportation and related risks, thieves, unauthorized cloning, etc. For this reason check of the goods before and after the displacement are very important. Furthermore, checks are important to fix the protection level based on the risk evaluations.

Nowadays the more diffused and used techniques to recognize and to control the identity of artworks include:

- microanalysis using various techniques, as optical microscopy, spectroscopy and diffractometry, SEM, TEM, SIMS, PIXE, microsond with synchrotron light, x-ray microanalysis, EDS-WDS, carried out using small or very small samples of the objects;
- tomographic techniques using high-frequency electromagnetic waves (x-ray) in transparency mode with plane or rotating scan;
- special controls, for example nuclear techniques, thermoluminescence, natural or induced radioactivity, etc., to recognize special features (age, composition, etc.) of analyzed pieces.

All these methods have different disadvantages, some of which do not permit to obtain a reliable and univocal identification of the artifact. In fact, they have drawbacks linked to the small size of the investigated volumes with low-representativeness problems, to their generally high cost and to their generally high invasivity even if on very small samples.

Non invasive identification tools include survey techniques regarding:

- aspect, shape and dimensions of the artifacts, by means of instrumentation used in photography, microphotography and laser imaging;
- mass of the artifacts, by means of instruments like precision balances;
- color distribution of the artifacts, by means of instruments like those used in colorimetry.

Disadvantageously, all these non invasive techniques of identification are not so precise to identify univocally the artworks. In fact nowadays the laser technology or the multispectral reflectography permit to reproduce most of the features of the original artworks, including shape, dimension, weight, aspect, colors and texture, with the desired precision.

Furthermore, the state of the art takes account of many methods and apparatuses to realize a spectral analysis of vibrations induced in objects, with the aim of detecting internal defects or other features. But such methods and apparatuses are not suitable to be applied for the identification of the artworks, due to the fact that the used vibration source significantly affects the vibration spectrum, without assuring consequently the correct identification of the artifact in which vibrations are induced. Furthermore these methods, rather than to the identification of the artifacts, are aimed to the detection of internal defects, of different type (fractures, cracks, cavities, indentations): really, they are basically intended for the quality control of industrial items. An example of these methods is described in the U.S. Pat. No. 5,144,838 patent document.

Therefore there is a strong demand to realize an innovative method for recognizing and controlling the identity of the cultural artifacts, as well as an relative apparatus, that allows to overcome the above-mentioned inconveniences. The demanded method should get and give information on the physical state of the whole artifact.

SUMMARY OF THE INVENTION

Main purpose of this invention is to realize a method for the detection of a "sonic imprint" of three-dimensional objects, in particular artworks, absolutely non invasive and able to univocally identify any artifact characterized by a specific degree of rigidity.

A further purpose of the invention is to realize an apparatus, cheap and simple to be used, for the detection of said sonic imprint.

Therefore this invention aims to reach the above mentioned purposes by realizing a method for detecting a sonic imprint of three-dimensional objects, in particular artworks, wherein there is provided a plurality of vibration detecting means, firmly fixed in predetermined detection points on the external surface of the object, the method comprising according to claim 1 the following steps:

a) induction of vibrations in the object by means of a source of mechanical strain in a point of predetermined application points for the application of said strain;
b) acquisition of analogical signals coming from said detecting means and conversion of the signals from analogical to digital ones;
c) repetition of the steps a) and b) for a predetermined number of times;
d) repetition of the steps a) to c) for the remaining predetermined application points for the application of the strain;
e) spectral analysis of resonance frequencies for each of the detecting means and for each set of inductions of vibrations in a same application point for the application of the strain;
f) normalization of the frequency spectra, comparison of the normalized spectra and selection of one or more groups of normalized spectra which are similar each other;
g) processing of the average of the one or more groups of similar normalized spectra, obtaining one or more normalized averaged spectra defining the sonic imprint of the object.

A further aspect of the invention is to provide an apparatus for the detection of a sonic imprint of three-dimensional objects, suitable to carry out the mentioned method which, accordingly to claim 6, comprises a source of mechanical strain, suitable to induce vibrations in the object to be analyzed; a plurality of detecting means for detecting vibrations; fixing means for fixing said detecting means on the surface of the object in predetermined detection points; acquisition means for acquiring analogical signals, connected with the detecting means, suitable to convert said analogical signals in digital signals; processing means for said digital signals, suitable to carry out the steps from e) to g).

The "sonic imprint", obtained with the method and the relative apparatus of the present invention, is practically "unique"; in fact, it is a characteristic univocally linked to any physical object able to vibrate, i.e. characterized by rigidity and elastic behavior of the material, and not very quickly time-changing. Two artworks, appearing to be identical, are different indeed at least for their internal defects that more or less alter the sonic imprint. In fact, it is sufficient to consider that some musical instruments that people have wanted to clone for a long time, like Stradivari violins, in spite of numberless technological efforts, cannot be reproduced with the same sound, i.e. with the same vibration frequencies.

A further advantage is represented by the fact that the sonic imprint is representative of the whole object and not of an only small or very small part of it, as it would be the case for a microanalysis regarding a small fragment of the object.

Furthermore, the appropriate choice of many detection points and application points where respectively the detectors and the source or sources of strain have to be placed on the external surface of the object, covering most of the external surface of the object approximately following its geometrical symmetry, allows obtaining a quasi-independence of the sonic imprint from the locations of these points. The quasi-independence means that all the normal vibrational modes have been excited and then the number of detectors or transducers allows recognizing all of them. For this purpose when the energy source or strain source is external to the object (i.e. at a certain distance from the surface, like it is possible to obtain using a driven loudspeaker or a generator of acoustic pulses) many relative source-object positions can be used or a relatively high source-object distance to uniformly hit the object. Nevertheless, a very different choice can be made selecting a limited number of detection points and application points (in the extreme case of one source and one detector, the only advantage being the simplicity of the required instrumentation and the short time required for acquisition and processing of the experimental data), but in this cases the locations of detection points and application points can be critical, so that the repeatability of these sonic imprints could become strongly dependent on the exact locations of the detection points and application points.

The increase of the number of detection points and application points rises the number of information about the object. But, if the detectors are 1D (or 2D) and they are located on different directions (or planes), obviously the detected vibration components can give different results, also depending on the symmetry of the object. Therefore the increment of the number of detectors should be made taking into account this directional problems, sometimes bringing to the definition of two or more different signatures, i.e. averaged normalized spectra, composing the sonic imprint.

It is important to stress that, due to complexity of the 3D vibration movements, the sonic imprint could depend on the type of used detectors (1D, 2D or 3D) and on their transduction characteristics, so that it is important to use the same type of detectors to compare different sonic imprints of the same object.

An analysis of the geometry of the object to be investigated is useful for the selection of a predetermined set of detection points, useful to locate the vibration detecting means, and of a predetermined set of application points to locate strain inductors or of application positions to locate far strain sources.

In view of the successive controls of the sonic imprint it is important to memorize, for example by means of pictures, the points of the surface which have been selected and used as detection points and application points.

The method of the invention can be used to detect the possible time variations of the sonic imprint, both the very slow variations, linked to the unavoidable decay of the mechanical properties of the object, and the faster ones, due to a sudden decay, for instance caused by cracks, fractures, imbibitions, etc.

As precious artifacts are very frequently displaced everywhere for exhibitions and shows, the application of the method, carried out before and after the displacement, can be very useful to detect eventually occurred damages. Advantageously, the sonic imprint measurement can be carried out even by not very specialized personnel.

This is a distinction point with respect to other methodologies requiring higher technical competences, like x-ray, laser scanner, spectrophotometry, etc.

Furthermore, detection of sonic imprint, by using the method and the apparatus of the invention, is rather quick. The time needed for the detection can range between few tens of minutes and few hours, depending on the shape and dimensions of the analyzed object.

Advantageously, the above described method also allows to construct an analogical "card" of an artwork, like the bar codes used for commercial purposes, by using a bar for each frequency of the at least one averaged normalized spectrum defining the sonic imprint. Therefore, with the method of the invention it is possible to carry out a systematic control of the artworks kept in the museums, with a consequent substantial enrichment of the technical cards.

The dependent claims describe preferred embodiments of the invention.

BRIEF DESCRIPTION OF THE DRAWINGS

Further characteristics and advantages of the invention are more evident in the light of the detailed description of a preferred, but not exclusive, embodiments of a method and relative apparatus for the detection of the sonic imprint, illustrated by way of non-limitative example with reference to the accompanying drawings, in which:

FIG. 1 represents some components of the apparatus according to the invention;

FIG. 2 represents a vessel on which other components of the apparatus of the invention are applied according to an operating mode;

FIG. 3 represents a dish on which the same components visible in FIG. 2 are applied according to another operating mode;

DETAILED DESCRIPTION OF PREFERRED EMBODIMENTS OF THE INVENTION

Figure 4:
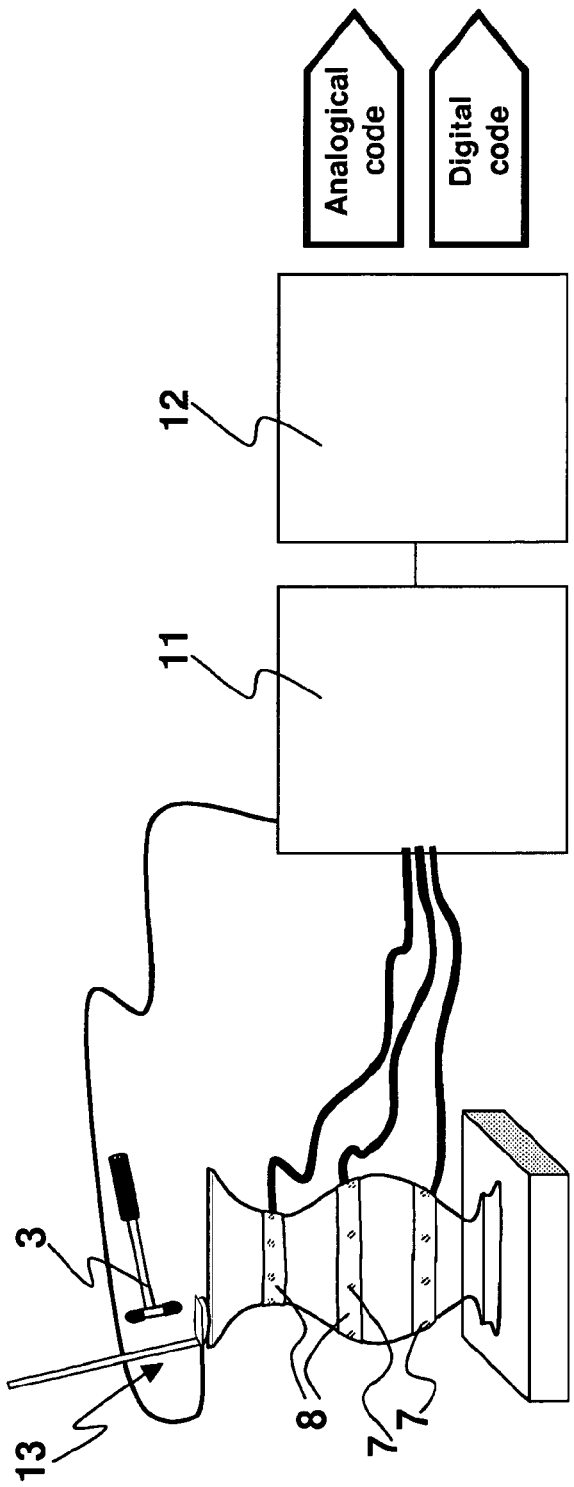
FIG. 4 represents a schema of the apparatus of the invention.
Figure 5:
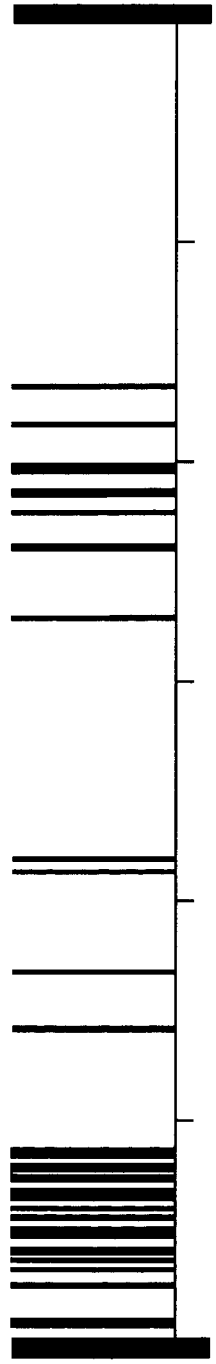
FIG. 5 represents an example of a vibrational analogical bar code obtained with the method of the invention.

The method of the present invention allows the identification of some physical characteristics of objects made of different types of material—namely natural or artificial lapideous, metallic, glass, crystal, wood, corneous, etc. —by means of the detection technique of the free or forced vibrations, following a mechanical strain or during the application of a driving force, and the successive analysis of the vibration frequencies in order to recognize the resonance frequencies. In such a way the object can be identified in univocal and certain way, monitoring the possible time decay of the mechanical characteristics as well as its integrity.

The vibrational movements of an object depend on the geometrical shape of the object, on its physical composition, on the elasticity modules and its internal defects, which are unique for each piece to analyze, especially if it is handmade.

The analysis of resonances allows to obtain, by means of the method of the invention, a vibrational code obtained starting from an averaged normalized frequency spectrum. This vibrational code represents what here is called "sonic imprint" of the object. For lapideous artifacts equal or larger than about 0.01 cubic meters, the interesting frequencies are preferably comprised in the range 0-6000 Hz, also depending on the geometry of the artifact and on its eventual internal discontinuities. For small objects, having a volume lower than 0.01 cubic meters, of for small protuberances of big objects some resonance frequencies can rise up to 10000-12000 Hz.

An apparatus suitable to carry out the method, object of the present invention, for detecting the sonic imprint of objects like, for example, statues, vessels, dishes, furnishings, etc., comprises:

- an energetic source for generating a mechanical strain suitable to excite vibrations in the object to be analyzed;
- a plurality of detecting means for detecting vibrations, to be firmly fixed on the external surface of the object to be analyzed, having very small mass and dimensions, definitely negligible with respect to those of said object;
- fixing means for fixing said detecting means on the surface of the object, having very small mass, definitely negligible with respect to the mass of said object;
- acquisition means for acquiring analogical signals coming from the detecting means, suitable to carry out the A/D conversion with suitable sampling rate (minimum 40 kHz) and resolution (minimum 16 bit);
- possible control means for controlling the break-time of the strain induction, in order to trigger the start of analogical signal acquisition;
- processing means for processing the digital signals, for calculating the sonic imprint as well as for representing it and, eventually, for comparison with the sonic imprints previously detected on the same object.

The source of mechanical strain can be constituted, for example, by a simple hand-driven gummed hammer.

Alternatively, such strain source can be made, for example, by a mechanical vibrator or by a loudspeaker driven by a suitable electrical signal with a power amplification.

Advantageously, the source of mechanical strain is impulsive-type or vibrational-type with a frequency changer.

The mechanical vibrator and the loudspeaker are suitable not only for generating impulsive strain but also for generating driving forced vibrations. Used as impulsive source, they can be useful to detect the free damped vibrations of the object, so that the detection of the sonic imprint is made in time-domain. On the contrary, if the sources are used to induce forced vibration at various frequencies, the detection of the sonic imprint can be made in frequency-domain.

Advantageously strain sources, like a loudspeaker, can be also used at a certain distance from the object, especially if the emitted energy is sufficiently high. In this case the non invasivity of the method is absolutely assured.

When an impulsive source is used, means for controlling the starting time of the acquisition of signals (break-time) is very useful, too. This control means can be made with a mechanical or electronic trigger, to be used for the time-domain detection. On the contrary, trigger can be unnecessary for frequency-domain detection.

If a gummed hammer 3 is used as an impulsive source, the trigger 13 can comprise a metallic plate 1 on which the hammer 3 is hit, as illustrated in FIG. 1. Such a plate 1 has on its upper surface a lamella 2 which, hit by the hammer 3, closes an electric circuit in order to operate as a trigger giving the time-break. Plate 1 preferably has a gummed lower surface 5.

The trigger can be provided with a handle 4 to make easy its leaning against the object to be analyzed and to assure the adhesion to the object surface during the striking. The plate 1 is preferably circular with a diameter of 2-3 cm; the handle 4 is preferably 20 cm long and 1 cm large.

The detecting means, that must be firmly fixed to the surface of the analyzed object, can comprise piezoelectric or electro-magnetic or capacity transducers of higher quality. Advantageously, all the transducers should be characterized by a transduction factor equal or very similar to each other as well as practically constant at every frequency in the range from 0 to 15000 Hz. Furthermore they have to be stable (high durability).

The number of transducers used to identify the sonic imprint of the objects can range from four, in the case of very small objects having linear dimensions up to 20 cm, to sixteen, for objects with linear dimension of the order of 1 m, especially if the shape is complex, like the statues. With relation to the geometric characteristics of the object to be analyzed, the number of the transducers can also be larger.

Advantageously, transducers have a weight equal or lower than 1 g, so that practically they not alter the space distribution of the masses and, consequently, the vibration response to the mechanical strains. Among the different types of transducers or detectors it is preferred to use very effective accelerometers sensitive to radial movements like, for example, the piezotite ceramic dishes, particularly light (weight lower than 1 g) and thin (thickness is about 2 mm). Alternatively, piezoelectric or magnetic sensors can be used, like the LP gramophone stylus.

For the firm fixing of transducers to predetermined points of the surface of the analyzed object, elastic strips and/or plastic grippers can be advantageously used. Both strips and grippers should be very light so that practically they not alter the space distribution of the masses, and consequently the vibrational response to the mechanical strains. Preferably, elastic strips or bandages few centimeters large, for example 4-6 cm, are used, with an elastic expansion of 150-250%. Near the borders or for objects with a flat shape (dishes, vessels, etc.) grippers constituted, for example, by simple cut plastic rings are preferably used, said rings having diameter from 5 to 8 cm and section equal to about 10-20 $mm^2$, stretchable in order to recover the pressure necessary to firmly fix the transducers to the object surface.

As an example, FIG. 2 shows a vessel 6 on which transducers 7 are fixed by means of elastic strips 8. Differently, FIG. 3 shows a dish 9 on which transducers 7 are fixed by means of ring shaped grippers 10.

Transducers 7, that vibrate with the object, are connected to the acquisition means comprising a multi-channel acquisition card 11, with a number of channels equal or higher than the number of transducers. Every acquired analogical signal is then converted by the card to digital signal, with a sampling frequency of at least 40 kHz in order to assure a reliable fidelity up to frequencies of 15 kHz, and saved. The acquisition card 11 is provided with an input for trigger 13, in order to acquire signals in time-domain, so that recording of the signals can be synchronized with the hitting time, i.e. the instant of closing of the aforesaid circuit.

After acquiring the digital signals with the acquisition means 11, the processing means 12, cooperating with said acquisition means and comprising a dedicated software, carry out the following steps:

- analysis of the variability among different signals acquired in the same conditions (from a same source or application point to a same transducer or detection point) in order to recognize eventual anomalous signals, due to a bad strain induction and/or a very noised range of time;

denoising of the acquired signals, for each transducer, in order to minimize the environmental random noise using a special technique of stacking, that is a kind of averaging process (same source and same transducer) improving the signal to noise ratio by means of a "stacking" operator;

analysis of the spectrum of the resonance frequencies for each transducer and for each set of application points where strains have been applied. In order to assure an accurate evaluation of the sonic imprint, the frequency sampling of the spectrum has to be calculated at least every 1 Hz.

If the acquisition is carried out in time domain, this can be advantageously carried out by means of an appropriate increase of the source power inducing the strain and the recording time range and/or a successive appropriate processing of the signals.

If the acquisition is carried out in frequency domain, the frequency sampling should be fine enough to reach this resolution (1 Hz).

Appropriate techniques should be advantageously used to reduce also the noise in the spectra: in particular, noise should be recorded immediately before and/or after the induced vibration period, in order to evaluate the noise spectrum and possibly appropriately remove it from the spectra of acquired signals;

normalization of the spectra and comparison of the normalized spectra in order to obtain one group of normalized spectra; advantageously, for each spectrum the normalization should be made using as weight the value of the area of the spectrum. In fact, in this way, the sharp maxima are better evidenced and evaluated in the resonance frequencies selection;

cross-correlation of all the normalized spectra. This operation is aimed to the eventual subdivision of the normalized spectra in groups characterized by different frequency peaks depending on the positions of the detection points or of the application points. This cross-correlation advantageously facilitates the possible selection of two or more groups of normalized spectra which are similar each other. This occurrence is typical of objects having particularly anisotropic elastic characteristics, like the wooden artworks;

processing of the average of the one or more groups of similar normalized spectra, obtaining one or more normalized averaged spectra defining the sonic imprint of the object;

coding of each averaged spectrum of the resonance frequencies.

In particular the step of processing of the average of the one or more groups of similar normalized spectra and the identification of the relative resonance frequencies can be carried out, for each group of normalized spectra, in two different ways, approximately giving the same results:

1) all the normalized spectra are used to calculate a averaged normalized spectrum. Then, all the relative maxima of the averaged spectrum are considered. Each of maxima is confirmed if the maximum value is higher than the neighboring values in the range of 10 Hz, with a difference of minimum 10% of the background, elsewhere it is ignored. A final confirmation is given after controlling the presence of each of maxima, within ±5 Hz error, in at least 60% of the signals. The confirmed maxima identify the resonance frequencies and constitute the definitive spectrum of the "sonic imprint". Besides the values of the component frequencies, the spectrum is characterized by the standard deviation of each of component frequencies (calculated using all the signals in which it is present) as well as all the set of information regarding the location of transducers and type and position of the energy source;

2) all the normalized spectra are analyzed in order to select the frequencies of the significant maxima in the spectra, being said significant maxima those values higher than the neighboring values in the range of 10 Hz, with a difference of minimum 10% of the background.

Therefore, a cross-correlation analysis among all frequencies sets of the averaged spectra is performed to construct a final set of resonance frequencies (at a 60% level of presence) as well as their standard deviations. Repeated frequencies and their standard deviations, as well as all the set of information regarding the location of transducers and type and position of the energy source, constitute the definitive spectra of the sonic imprint.

This second procedure is more time-consuming, but it gives finer results.

All the frequencies contained in the one or more averaged normalized spectra are associated with the possible error (standard deviation) that, with the method and apparatus of the invention, is advantageously limited to a maximum of 2%.

Coding of the averaged spectrum of the resonance frequencies can advantageously be made with the construction of an analogical bar code to be associated to the same object. In the case of more than one averaged spectrum, more than one bar code can be appropriately associated to the object. In particular, this can be the case when the objects are geometrically very complicated and/or constituted by different materials.

The analogical bar code can be realized by means of a transposition of the averaged spectrum in terms of vertical bars having the same height and a different thickness. The thickness of each bar can be associated with the amplitude of the corresponding component in the normalized spectrum or to the probable error (standard deviation) connected with the considered resonance frequency. In the first case (thickness associated with the amplitudes), for example, after normalization the frequency with maximum amplitude (main resonance frequency) is associated with thickness 1 mm, the other resonance frequencies having thickness between 0.1 mm and 1 mm. One example of this type of code is given in FIG. 2, and has the following characteristics:

a predetermined width, for example 12 cm, which is linearly proportional to the frequency range between 0 and 6 kHz (1000 Hz correspond to 2 cm);

a predetermined height, for example 2 cm;

the thickness of each bar is proportional to the amplitude of the corresponding resonance frequency in the normalized spectrum, for example the thinner one is 0.2 mm thick and the larger one is 1 mm.

On the analogical bar code, all the resonance frequencies are included with their corresponding relative amplitudes appropriately subdivided in "graphical classes". For example:

if the frequency amplitude is larger than 10% of the maximum amplitude, its bar is 0.2 mm thick;

if the frequency amplitude is larger than 20% of the maximum amplitude, its bar is 0.3 mm thick;

if the frequency amplitude is larger than 30% of the maximum amplitude, its bar is 0.4 mm thick;

if the frequency amplitude is larger than 40% of the maximum amplitude, its bar is 0.5 mm thick;

if the frequency amplitude is larger than 50% of the maximum amplitude, its bar is 0.6 mm thick;

if the frequency amplitude is larger than 60% of the maximum amplitude, its bar is 0.7 mm thick;
if the frequency amplitude is larger than 70% of the maximum amplitude, its bar is 0.8 mm thick;
if the frequency amplitude is larger than 80% of the maximum amplitude, its bar is 0.9 mm thick;
if the frequency amplitude is larger than 90% of the maximum amplitude, its bar is 1 mm thick.

Advantageously, a different bar code, obtained considering the probable errors instead of the amplitude of the various frequency components, can be constructed analogously, taking into account the associated probable errors rather than the amplitudes. The two bar codes, having the thickness of the bars respectively related to their amplitudes or errors, can be advantageously composed to form a double bar code, characterized by a higher information content.

The "analogical" bar code may also be confined by two lateral bars, for example 1.2 mm thick, which can be useful for controls using an optical reader.

The "analogical" bar code is advantageous to quickly check the identity of the object. In fact, a specialized technician can recognize the identity of the object by a quick visual comparison of the bar code with the previously saved one; if there is not a previously saved code, the bar code can also be useful to roughly evaluate some general characteristics of the object (for example, dimensions, material, internal discontinuities, etc.).

In order to save in the archives data having more precision and details on the analyzed artwork, coding of the spectrum can be advantageously transferred to a cryptic digital bar code and inserted in a RFID chip, that can contain all the values of the resonance frequencies and the relative amplitudes, as well as their standard deviations. The RFID chip is very useful for an easy and precise fruition of the archived data. In this case the precision is much higher than that of the analogical bar code: frequencies and relative amplitudes are evaluated respectively with the precision of 1 Hz (for frequencies, 5 4 digits) and with two digits for percent amplitudes (from 1 to 99%), while the probable errors can be given with a sensitivity of 0.1 Hz (for errors, 3 digits). For instance, for objects showing up to thirty resonant frequencies, the cryptic code of its averaged spectrum, including some general data, should contain a maximum of 350 characters: number of frequencies, their values, probable errors and relative amplitudes. However, the code can be cryptic to improve safety and secrecy of the precise identification.

The described apparatus allows to carry out the sonic imprint detection of a three-dimensional artwork, in the time-domain, with the following steps:

1) firm fixing of transducers by means of the mentioned fixing means in predetermined detection points of the external surface of the artwork, to acquire the vibration modes;
2) induction of vibrations in the artwork by means of the source of mechanical strain in one of the predetermined application points or positions for the application of the strains ("strain-positions");
3) acquisition of the analogical signals coming from all the transducers, by means of the multi-channel acquisition card, with a triggered starting time, and conversion of the signals from analogical to digital;
4) Repetition of the induction of vibrations (step 2), preferably from 3 to 10 times, in order to apply a stacking procedure;
5) Repetition of the steps 2) to 4) for the remaining predetermined application points;
6) processing of all the acquired digital signals, carrying out via software all the steps previously described, until the evaluation of the resonance frequencies is carried out and coding of each averaged normalized spectrum of the resonance frequencies, i.e. coding of the sonic imprint of the artwork, is saved.

If the strain source is a gummed hammer, advantageously, in the step 6) of signal processing, the first part of the acquired signals (only few milliseconds, after a preliminary automatic control) is eliminated due to some influences given by the possible differences in beating. If the strain source is a loudspeaker, few milliseconds should be eliminated to take into account possible differences in the direct strain given by the loudspeaker to some transducers.

In the case that the detection of the sonic imprint is carried out in frequency-domain the step 2) includes the induction of vibrations by means of a strain source at slowly-variable frequencies, starting from few Hz to the maximum forecast resonance frequencies, that obviously depend on the characteristics of the artworks, mainly its size and relative dimensions.

A mechanical vibrator with variable frequency can be used or, preferably, a power loudspeaker driven by a sweep of constant power and variable frequencies from 0 to 6000 Hz, or more if it is needed. The frequency variability is advantageously slow—for instance sweep of 12-24 seconds—and accurately controlled.

In this case the step 3) of acquisition of analogical signals coming from the transducers is started up before the induction of the sweep, or by hand or by means of a switch-trigger, and has a duration a little longer than the time range of the sweep; furthermore, step 6) of processing of digital signals is applied to all the range of the sweep by analyzing, frequency per frequency, each of channels (transducers).

Before carrying out the detection method of the invention it is preferable to put the artwork to be analyzed on a polystyrene sheet or other suitable material able to damp vibration and to de-couple the transmission of vibrations to the soil or other connected masses, that can influence the vibrational response of the artwork. Alternatively, the artwork can be leaved on its usual basement, for instance that used for the exposition in the museum, provided that detection of the sonic imprint is repeated always in the same conditions (including also the same coupling conditions). But in this case the artwork to be analyzed practically becomes a couple of objects, artwork and basement linked together.

Therefore, the method and the apparatus of the herein invention allow to univocally identify the analyzed object by means of the "sonic imprint", i.e. an accurate sonic analysis. The method utilizes the fact that the normal vibration modes of the objects to be analyzed are unequivocally well established by the physical properties (geometrical, mechanical, elastic properties, distribution of masses and physical defects) of the same objects.

The comparison of the sonic imprint obtained on an artwork with the previous one saved in the archive, if the artwork has been previously analyzed, allows easily and quickly to verify the authenticity of the artwork.

The invention claimed is:
1. Method for detecting a sonic imprint of a three-dimensional object, wherein there is provided a plurality of vibration detecting means, firmly fixed in predetermined detection points on the external surface of the object, the method comprising the following steps:
a) induction of vibrations in the object by means of a source of mechanical strain in a point of predetermined application points for the application of said strain;

b) acquisition of analogical signals coming from said detecting means and conversion of the signals from analogical to digital ones;
c) repetition of the steps a) and b) for a predetermined number of times;
d) repetition of the steps a) to c) for the remaining predetermined application points for the application of the strain;
e) spectral analysis of resonance frequencies for each of the detecting means and for each set of inductions of vibrations in a same application point for the application of the strain;
f) normalization of the frequency spectra, comparison of the normalized spectra and selection of one or more groups of normalized spectra which are similar each other;
g) processing of the average of the one or more groups of similar normalized spectra, obtaining one or more normalized averaged spectra defining the sonic imprint of the object;
wherein there is provided a coding of said one or more normalized averaged spectra, having as output a digital cryptic bar code and/or an analogical bar code.

2. Method according to the claim 1, wherein the digital bar code is inserted in a RFID chip.

3. Method according to claim 1, wherein before the step e) there is provided a processing of the digital signals comprising a variability analysis of the signals acquired considering a same detection point and a same application point, in order to recognize eventual anomalous signals and improve the signal to noise ratio by means of a "stacking" operator.

4. Method according to the claim 1, wherein said predetermined number of times comprises 3 to 10.

5. Detection apparatus, suitable to carry out a method for detecting a sonic imprint of a three-dimensional object according to claim 1, comprising:
a source of mechanical strain, suitable to induce vibrations in the object to be analyzed;
a plurality of detecting means for detecting vibrations;
fixing means for fixing said detecting means on the surface of the object in predetermined detection points;
acquisition means for acquiring analogical signals connected with the detecting means, suitable to convert said analogical signals in digital signals;
processing means for processing said digital signals, suitable to carry out the steps from e) to g) of said method,
wherein said source of mechanical strain is a generator of acoustic pulses that can be used at a predetermined distance from said object,
and wherein there are provided control means for controlling the time in which vibrations are induced, said control means being connected with said acquisition means in order to trigger the start of signal acquisition.

6. Apparatus according to claim 5, wherein the source of mechanical strain is impulsive-type or vibrational-type with a frequency changer.

7. Apparatus according to claim 5, wherein the detecting means comprise piezoelectric or ceramic or electromagnetic detectors.

8. Apparatus according to claim 5, wherein said fixing means comprise elastic strips and/or plastic grippers.

9. Method for detecting a sonic imprint of a three-dimensional object, wherein there is provided a plurality of vibration detecting means, firmly fixed in predetermined detection points on the external surface of the object, the method comprising the following steps:
a) induction of vibrations in the object by means of a source of mechanical strain in a point of predetermined application points for the application of said strain;
b) acquisition of analogical signals coming from said detecting means and conversion of the signals from analogical to digital ones;
c) repetition of the steps a) and b) for a predetermined number of times;
d) repetition of the steps a) to c) for the remaining predetermined application points for the application of the strain;
e) spectral analysis of resonance frequencies for each of the detecting means and for each set of inductions of vibrations in a same application point for the application of the strain;
f) normalization of the frequency spectra, comparison of the normalized spectra and selection of one or more groups of normalized spectra which are similar each other;
g) processing of the average of the one or more groups of similar normalized spectra, obtaining one or more normalized averaged spectra defining the sonic imprint of the object;
wherein before the step e) there is provided a processing of the digital signals comprising a variability analysis of the signals acquired considering a same detection point and a same application point, in order to recognize eventual anomalous signals and improve the signal to noise ratio by means of a "stacking" operator.

* * * * *